United States Patent [19]
Graichen

[11] Patent Number: 6,096,244
[45] Date of Patent: Aug. 1, 2000

[54] MELAMINE-POLYCARBOXYLIC ACID AMIDES AND THEIR USE AS ANTICORROSIVE AGENTS

[75] Inventor: Stefan Graichen, Hammersbach, Germany

[73] Assignee: ZTS-Chemie GmbH, Langenselbold, Germany

[21] Appl. No.: 09/039,507

[22] Filed: Mar. 13, 1998

[51] Int. Cl.$^7$ ...................................................... C09K 3/00
[52] U.S. Cl. .......................... 252/392; 544/196; 544/198; 544/200
[58] Field of Search ............................ 252/80, 390, 392; 544/196, 198, 200

[56] References Cited

U.S. PATENT DOCUMENTS

| | | | |
|---|---|---|---|
| 2,485,309 | 10/1949 | Nunn | 252/392 |
| 4,402,907 | 9/1983 | Clark | 422/7 |
| 5,152,929 | 10/1992 | Bentley et al. | 252/391 |
| 5,347,008 | 9/1994 | Bentley et al. | 548/170 |

FOREIGN PATENT DOCUMENTS

| | | |
|---|---|---|
| 2066806 | 10/1992 | Canada . |
| 0 041 039 | 5/1981 | European Pat. Off. . |
| 0 398 284 | 11/1990 | European Pat. Off. . |
| 0 541 966 | 10/1992 | European Pat. Off. . |
| 0 565 774 | 11/1992 | European Pat. Off. . |
| 0 553 962 | 4/1993 | European Pat. Off. . |
| 0 554 023 | 8/1993 | European Pat. Off. . |

OTHER PUBLICATIONS

Y.W Ca O. *Thin Solid Films,* 284–285 (1996) 859–862, 1996.
Chemical Abstract No. 126: 52 559: A novel amphiphilic ferrocene derivative containing a barbituric acid unit: synthesis and Quadratic optical non–linearity; *Thin solid Films* (1996), 284–285, 859–862.
Chemical Abstract No. 124: 94 444: Recognition–improved monolayer formation on air–water inferface; *Chin. J. Chem.* (1995), 13(5), 385–90.

*Primary Examiner*—Gabrielle Brouillette
*Assistant Examiner*—Cephia D. Toomer
*Attorney, Agent, or Firm*—Kenyon & Kenyon

[57] ABSTRACT

The present invention relates to a melamine-polycarboxylic acid amide and its use as a corrosion protection agent. Specifically, a melamine-polycarboxylic acid amide having a particular Formula I

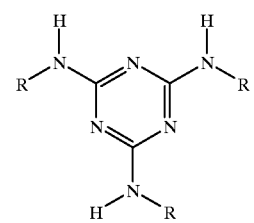

(I)

as well as alkali, ammonium, and amine salts thereof.

20 Claims, No Drawings

MELAMINE-POLYCARBOXYLIC ACID AMIDES AND THEIR USE AS ANTICORROSIVE AGENTS

FIELD OF THE INVENTION

This invention concerns melamine-polycarboxylic acid amides and their use to inhibit corrosion of iron or iron-containing metals in contact with aqueous systems.

BACKGROUND OF THE INVENTION

It is known that considerable efforts have been expended to reduce corrosion in metals. Thus, the use of triazinecarboxylic acids has been proposed in European Patent 46 139 as corrosion inhibitors for aqueous systems in contact with iron or iron-containing metals. European Patent 511 163 discloses fluid aqueous dispersions containing a solid polycarboxyltriazine acid corrosion inhibitor. Furthermore, U.S. Pat. No. 4,402,907 and European Patent A-129 506 disclose the suitability of certain heterocyclic polycarboxylic acids as corrosion inhibitors for aqueous systems in contact with metals, which can be used in aqueous systems, for example, in cooling water systems, steam generating systems, metal-working means, and aqueous hydraulic fluids. Since most polycarboxylic acids are only slightly soluble in water, the polycarboxylic acids are used in the form of their water-soluble salts, i.e., they are neutralized before use or added to a basic aqueous system. They are, however, usually stored and sold in the form of free polycarboxylic acids.

Free polycarboxylic acids are usually solid substances. They are normally isolated from an aqueous phase by filtration during manufacturing. The filtered product is generally rinsed with water and then dried. More recently, in order to save energy needed for drying, the wet filter cake, containing approximately 50% water, has been offered commercially for use in aqueous systems. The wet filter cake, however, has the disadvantage that it is not fluid. It cannot be poured or cast, but must be metered or refilled manually with the help of a scoop. Therefore it has also been suggested that polycarboxylic acids be used in the form of high-solids aqueous dispersions.

Melamine-based corrosion inhibitors are also known. Thus, U.S. Pat. No. 2,485,309 describes methylolmelamine condensation products, but these by no means meet today's strict requirements for a corrosion inhibitor.

Furthermore, Chemical Abstracts 126:52 599 and 124:98 444 disclose reaction products of one mole melamine with one or two moles of succinic acid. Their use as corrosion protection agents, however, is not mentioned.

OBJECTS AND SUMMARY OF THE INVENTION

It has now been observed that novel melamine-polycarboxylic acid amides and their water-soluble salts are excellent corrosion inhibitors in aqueous systems and are eminently suited for use in water circuits, aqueous machining fluids, antifreeze fluids, hydraulic fluids, or aqueous coatings.

The present invention provides is therefore melamine-polycarboxylic acid amides having Formula I:

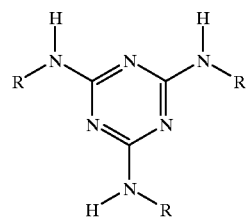

where at least one of the R radicals is a substituent having Structure II:

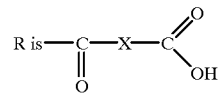

whose carboxyl group can be condensed with another melamine radical and X can be a straight-chain or branched alkylene or alkenylene radical with one to twelve carbon atoms, with the exception of ethylene, which may also contain a cyclopentylene, cyclohexylene, or phenylene group or is a

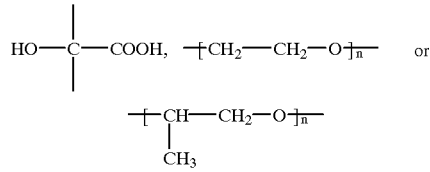

where n can assume values between 1 and 5, and the other radicals R denote hydrogen, as well as their alkali, amine, or ammonium salts.

DETAILED DESCRIPTION OF THE INVENTION

In the melamine-polycarboxylic acid amides according to this invention, the R radical can be derived from a saturated or unsaturated, straight-chain or branched dicarboxylic acid, for example, butanedioic acid, pentanedioic acid, hexanedioic acid, heptanedioic acid, nonanedioic acid, and preferably decanedioic acid. The carbon chain of these dicarboxylic acids may also contain a cyclopentylene, cyclohexylene, or phenylene radical. Citric acid or a dicarboxylic acid containing ethylene oxide or propylene oxide units also can be reacted with melamine to yield valuable corrosion protection agents according to this invention.

Particularly preferable are melamine-polycarboxylic acid amides in which all three amino groups are acylated. However, melamine derivatives where only one or two amino groups are acylated can also be used. Di- or tricarboxylic acids used for reacting with melamine are generally reacted with melamine in such ratios that at least one carboxyl group of the di- or tricarboxylic acid remains unreacted. The efficacy of the melamine-polycarboxylic acid amides according to this invention as corrosion protection agents is, however, not limited if part of the second carboxyl group of the dicarboxylic acids used forms an amide bond with another melamine molecule due to the use of an excess amount of melamine. However, at least 80%, preferably more than 90% of the di- or tricarboxylic acid structural units should still have a free carboxylic acid group, so that the melamine-polycarboxylic acid amides according to this invention can be dissolved in water forming salts.

Melamine-polycarboxylic acid amides are manufactured by melting the di- or tricarboxylic acid or the corresponding dicarboxylic acid halide, dicarboxylic acid anhydride or dicarboxylic acid ester in a heated reactor and subsequently mixing melamine into the melt under an inert gas blanket. In general, the molar ratio of the dicarboxylic acid or the dicarboxylic acid derivative to melamine is 3:1. It is, however, also possible to use greater amounts of melamine, so that not all amino groups of melamine are acylated.

The dicarboxylic acid or dicarboxylic acid derivative used for the reaction is preferably a homogeneous chemical compound. However, mixtures of different dicarboxylic acids can also be used if they have the structure defined by Structure II. A dicarboxylic acid useful to form the melamine-polycarboxylic acids in accordance with the present invention may be described by Formula (III):

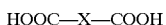   (III)

wherein X is as defined above.

A temperature between 120° C. and 180° C., preferably between 160° C. and 170° C., is maintained during the reaction. The reaction is normally completed after about 30 minutes. The reaction product can then be removed from the reactor after cooling and dissolved in an aqueous alkaline solution to form the corrosion protection agent. Any conventional alkaline media can be used to dissolve the melamine-polycarboxylic acid amides according to this invention. Triethanolamine is particularly preferred for forming salts.

An object of this invention is therefore a corrosion-protection agent containing a melamine-polycarboxylic acid amide of the Formula I:

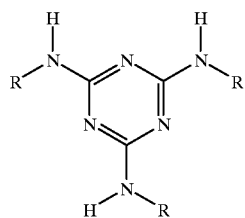

in an aqueous solution, in which at least one of the R radicals is a substituent having the Structure II:

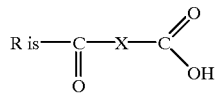

whose carboxyl group can be condensed with another melamine radical and X is a straight-chain or branched alkylene or alkenylene radical with 1 to 12 carbon atoms, which may also contain a cyclopentylene, cyclohexylene, or phenyl radical, or a

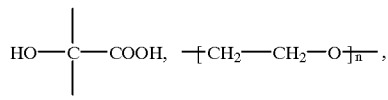

-continued

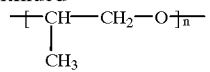

where n can assume values between 1 and 5, and the other R radicals denote hydrogen, as well as their alkali, ammonium, or amine salts.

The compounds having Formula I are preferably used in an amount of 0.001 to 5 wt. % in relation to the aqueous system. The aqueous system may be a water circuit, for example, a cooling water circuit, circuits of aqueous machining fluids such as cooling liquids for drilling, painting, cutting, turning, sawing, grinding, threading, rolling, or drawing of metals. Antifreeze compounds or glycol water-based hydraulic fluids, aqueous paints, such as dispersion paints or aqueous powder lacquers can also be provided with corrosion-protective properties using the melamine-polycarboxylic acid amides according to this invention.

The compounds having Formula I can be used in aqueous systems as sole additives or in combination with other additives. Examples of such co-additives in water circuits include known corrosion inhibitors such as phosphonates, phosphonocarboxylic acids or phosphinocarboxylic acids, N-acylsarcosines, imidazolines, triethanolamine, fatty acid amines or polycarboxylic acids. They can be copper passivators, such as water-soluble benzotriazoles, methylene-bis-benzotriazoles, or 2-mercaptobenzotriazoles. Furthermore, dispersing agents and carriers, such as poly (meth)acrylic acid and its salts, hydrolyzed polyacrylnitrile, polyacrylamide and its copolymers, lignin sulfonic acid and its salts, starch and starch derivatives, cellulose, alkylphosphonic acids, 1-aminoalkyl-1,1-diphosphonic acids and their salts, polymaleic acids and other polycarboxylic acids or alkaline phosphates can be added.

Additional co-additives may include precipitating agents such as alkali phosphates or alkali carbonates, oxygen-capturing agents such as alkali sulfates or hydrazine, complexing agents such as nitrilotriacetic acid or ethylenediamine-tetraacetic acid and their salts, or anti-foaming agents such as diamide distearyl sebacate, diamide distearyl adipate or ethylene oxide or propylene oxide condensation products of such amides, as well as fatty alcohols and their ethylene oxide condensation products.

Aqueous systems used as machining fluids may include water-dilutable cutting or grinding oils such as a) aqueous concentrates of melamine-polycarboxylic acid amide according to this invention with or without an antiwear additive, which can be used in a dilution of 1:50 to 1:100 as grinding fluid, b) polyglycols containing melamine-polycarboxylic acid amide, biocides, corrosion inhibitors and antiwear compounds, which can be used as cutting fluids in a dilution of 1:20 to 1:40 or grinding fluids in a dilution of 1:60 to 1:80, c) semisynthetic cutting oils on a similar basis as b), but also containing 10–25% of an oil, as well as sufficient emulsifying agent to keep the fluid transparent when diluted, d) emulsifiable mineral oil concentrates, which may contain a melamine-polycarboxylic acid amide, antiwear compounds, biocides, and/or antifoaming agents in addition to the emulsifying agent, and are normally diluted with water in a ratio of 1:20 to 1:50 to form an opaque emulsion, or e) product similar to d), but containing less oil and more emulsifying agent, providing transparent emulsions in a dilution of 1:50 to 1:100.

The compounds having Formula I can also be used in antifreeze compounds or hydraulic fluids alone or in combination with other additives. Other corrosion inhibitors may also be present, such as a) organic acids, their salts and esters, for example, benzoic acid, p-tert-butylbenzoic acid, disodium sebacate, triethanolamine-laurate, isononanic acid, triethanolamine salt of p-toluenesulfonamido-caproic acid, sodium-N-lauroylsarcosinate or nonylphenoxyacetic acid;

b) nitrogen-containing substances, such as fatty acid alkanolamides, imidazolines, oxazolines, triazoles or inorganic nitrites or nitrates;

c) phosphorus-containing substances, such as amine phosphates, phosphonic acids or inorganic phosphates, such as $NaH_2PO_4$; or d) sulfur-containing substances, such as salts of petroleum sulfonates, or heterocyclic compounds such as sodium-mercaptobenzothiazole.

The melamine-polycarboxylic acid amides according to this invention can be used in an aqueous-alkaline solution with a pH greater than 8.0 or as fluid aqueous dispersions. Suitable dispersing agents include all surface-active agents, in particular anionic and non-ionic surfactants. Such dispersions can be stabilized using thickeners with modified polysaccharides mainly of the xanthan, alignate, guar, or cellulose type being used. These also include cellulose esters such as methyl cellulose or carboxylmethyl cellulose and heteropolysaccharides. In addition to dispersing agents and thickening agents, the dispersions according to this invention may also contain additional auxiliary agents, for example hydrotropic agents such as urea or sodium xylene sulfonate; antifreeze compounds such as ethylene or propylene glycol, diethylene glycol, glycerin or sorbite; or biocides such as chloracetamide, formaldehyde or 1-2-benzoisothiazoline-3-one or complexing agents. To produce dispersions, it is recommended that solid melamine-polycarboxylic acid amides be used as the starting material, the dispersing agents and the thickening agent, as well as (if needed) the desired amount of water and other additives be added, and the mixture be agitated until a fluid and homogeneous dispersion is obtained. The dispersions thus produced are stable for several months at room temperature and at temperatures up to 40° C. They preserve their fluidity and do not separate. This is an important characteristic for storing and transporting dispersions. For the use of dispersions, it is advantageous that they can be handled as liquids and dissolve rapidly in alkaline-aqueous systems.

The invention is now illustrated in detail using the following examples:

EXAMPLES

Example 1

Three moles of decanedioic acid are placed and melted in a reactor provided with an agitator. One mole melamine is mixed into the mixture at approximately 170° C. and heated for another 30 minutes. Then it is cooled and the precipitating solid is treated with a 85% solution of triethanolamine and water in an amount such that a solution containing 8% of the melamine-polycarboxylic acid amide according to this invention, 60% triethanol amine (85%) and 32% water is obtained.

Such a solution can be added in an amount of 3% to a grinding fluid, a cooling fluid, or an antifreeze compound as a corrosion inhibitor.

Example 2

The corrosion protection properties of melamine-polycarboxylic acid amides were determined according to DIN 51360, Part II. The corrosion markings on a round paper filter, produced by the effect of water made artificially corrosive on gray cast iron chips in the presence of melamine-polycarboxylic acid amides, served as a measure of corrosion. The test was conducted as follows:

1. One mole melamine was melted with 1, 2, or 3 moles of a di- or tricarboxylic acid either under vacuum or under an inert gas blanket at a temperature of about 200° C. or heated in the presence of a high-boiling solvent such as dioxane until the condensation reaction was completed. The melt was then cooled, broken up, and powdered, or the solvent used was distilled off. The melamine-polycarboxylic acid amide obtained was contained in the proportion of 8% to 10% in a corrosion protective agent, which also contained 60% pure triethanolamine (85%) and tap water.

2. In accordance with DIN 51360, Part II, 3% of the above-named corrosion protection agent was added to a beaker of water with a total hardness of 3.58 mmol, prepared from $CaCl_2 \times 6H_2O$ and $MgSO_4 \times 7 H_2O$, and gray iron chips, placed on a round paper filter in a Petri dish, were wetted with this solution. After a dwelling time of 2 hours at room temperature, the iron chips were removed from the paper filter, the paper filter was rinsed and dried, and then the degree of corrosion was determined visually according to the table of DIN 51360, Part II.

The following results were obtained:

Degree of corrosion of the melamine-polycarboxylic acid amide:

| Test # | melamine-polycarboxylic acid amide made from | pH of a 3% solution of the corrosion protection agent | Degree of corrosion (8%) | Degree of corrosion (10%) |
|---|---|---|---|---|
| 1 | 1 mol melamine + 3 mol decanedioic acid | 8.75 | 3 | 1 |
| 2 | 2 mol melamine + 5 mol decanedioic acid | 8.85 | 1–2 | 1 |
| 3 | 1 mol melamine + 3 mol terephthalic acid | 9.0 | 2–3 | 1 |
| 4 | Terephthalic acid (control) | 8.3 | 4 | 4 |
| 5 | 1 mol melamine + 2 mol glutaric acid | 8.75 | 2–3 | 2 |
| 6 | 2 mol melamine + 5 mol glutaric acid | 8.87 | 1–2 | 1 |
| 7 | 1 mol melamine + 1 mol adipic acid | 8.2 | 2–3 | 1 |
| 8 | 1 mol melamine + 3 mol citric acid | 8.65 | 2 | 1 |

The table shows that good anticorrosive properties can be obtained with all the melamine-polycarboxylic acid amides according to this invention, which can be further improved if the melamine-polycarboxylic acid amide is contained in the corrosion protection agent in a higher concentration, for example, at 10%. Also noteworthy is the improved corrosion protection effect in the case of the more highly condensed products of tests No. 2 and 6.

What is claimed is:

1. A melamine-polycarboxylic acid amide having Formula I, as well as alkali, ammonium, and amine salts thereof:

(I)

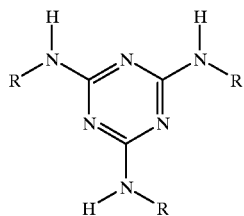

wherein 1, 2 or 3 of the R radicals have Structure II:

(II)

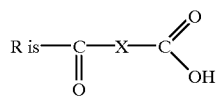

wherein the carboxyl group of Structure II is optionally condensed with another melamine radical and wherein X is a radical selected from the group consisting of methylene, a straight-chain alkylene radical with two to twelve carbons atoms, with the exception of ethylene, a branched alkylene radical with three to twelve carbon atoms, a straight-chain alkenylene radical with two to twelve carbons atoms, a branched alkenylene radical with three to twelve carbons atoms, any one of said X radicals containing a cyclo-compound selected from the group consisting of cyclopentylene, cylcohexylene, and phenylene,

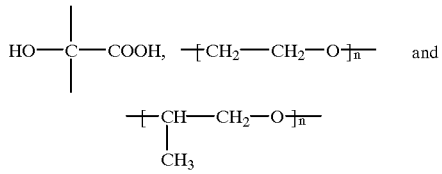

where n has a value between 1 and 5, and wherein 0, 1 or 2 of the R radicals are hydrogen.

2. The melamine-polycarboxylic acid amide according to claim 1 wherein at least one R radical is derived from a compound selected from the group consisting of decanedioic acid and citric acid.

3. A method for preparing a melamine-polycarboxylic acid amide having Formula I, as well as alkali, ammonium, and amine salts thereof:

(I)

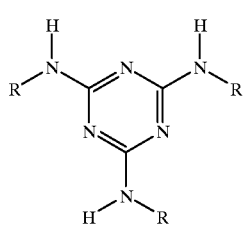

wherein 1, 2 or 3 of the R radicals have Structure II:

(II)

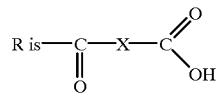

wherein the carboxyl group of Structure II is optionally condensed with another melamine radical and wherein X is a radical selected from the group consisting of methylene a straight-chain alkylene radical with two to twelve carbons atoms, with the exception of ethylene, a branched alkylene radical with three to twelve carbon atoms, a straight-chain alkenylene radical with two to twelve carbon atoms, a branched alkenylene radical with three to twelve carbon atoms, any one of said X radicals containing a cyclo-compound selected from the group consisting of cyclopentylene, cyclohexylene, and phenylene,

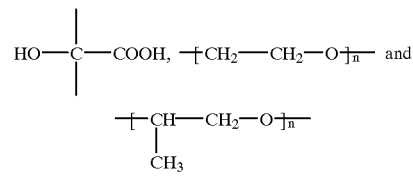

where n has a value between 1 and 5, and wherein 0, 1 or 2 of the R radicals are hydrogen, wherein the method comprises providing a melt of a compound selected from the group consisting of an acid having Formula III:

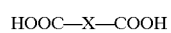 (III), acid halides of the compound of Formula III, acid anhydrides of the compound of Formula III, and esters of the compound of Formula III, and reacting said melt with melamine wherein X has one of the aforementioned meanings.

4. A corrosion protection agent, comprising:
water and an amount, effective to inhibit corrosion, of a melamine-polycarboxylic acid amide having Formula I, as well as alkali, ammonium and amine salts thereof:

(I)

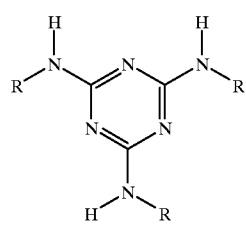

wherein 1, 2 or 3 of R radicals have Structure II:

(II)

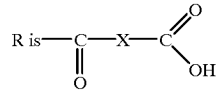

wherein the carboxyl group of Structure I is optionally condensed with another melamine radical, and wherein X is radical selected from the group consisting of methylene, a straight-chain alkylene radical with two to twelve carbon atoms, a branched alkylene radical with three to twelve carbon atoms, a straight-chain alkenylene radical with two to twelve carbon atoms, a branched alkenylene radical with three to twelve carbon atoms, any one of said X radicals containing a cyclo-compound selected from the group consisting of cyclopentylene, cyclohexylene, and phenylene,

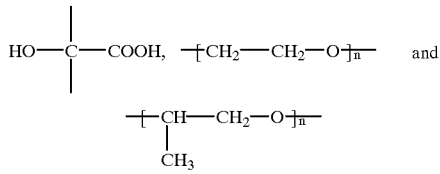

where n has a value between 1 and 5, and wherein 0, 1 or 2 of the R radicals are hydrogen, wherein the melamine-polycarboxylic acid amide is dissolved in the water.

5. The melamine-polycarboxylic acid amide according to claim 1, wherein at least one R radical is derived from a compound selected from the group consisting of butanedioic acid, pentanedioic acid, hexanedioic acid, heptanedioic acid, nonanedioic acid, and terephthalic acid.

6. The melamine-polycarboxylic acid amide according to claim 1 wherein 3 of the R radicals have Structure II.

7. The melamine-polycarboxylic acid amide according to claim 1 wherein 2 of the R radicals have Structure II.

8. The melamine-polycarboxylic acid amide according to claim 1 wherein 1 of the R radicals has Structure II.

9. The corrosion protection agent according to claim 4 wherein the melamine-polycarboxylic acid amide is provided in the corrosion protection agent at a concentration ranging from 0.001 to 5 wt. %.

10. The method of claim 3 wherein the molar ratio of the dicarboxylic acid having Formula III to melamine is about 3:1.

11. The method of claim 3 wherein the melt has a temperature ranging from 120° C. to about 200° C.

12. The method of claim 3 wherein the acid is a dicarboxylic acid.

13. The method of claim 12 wherein the dicarboxylic acid is selected from the group consisting of decanedioic acid, butanedioic acid, pentanedioic acid, hexanedioic acid, heptanedioic acid, nonanedioic acid, and terephthalic acid.

14. The method of claim 3 wherein the acid is citric acid.

15. The corrosion protection agent of claim 4 further comprising triethanolamine.

16. A method of forming a melamine-polycarboxylic acid amide wherein about 3 moles of decanedioic acid are melted in a reactor and whereby about one mole melamine is mixed into the melt at about 170° C. and heated for about 30 minutes.

17. The method of claim 16 wherein the melamine-polycarboxylic acid amide is treated with triethanolamine and water such that a solution containing about 8% of the melamine-polycarboxylic acid amide, about 60% triethanol amine and about 32% water results.

18. A method for preparing a melamine-polycarboxylic acid amide comprising the steps of:

providing melamine, providing an acid selected from the group consisting of dicarboxylic acid and tricarboxylic acid, reacting about 1 mole melamine with an amount selected from the group consisting of about 1 mole of dicarboxylic acid, about 2 moles of dicarboxylic acid, about 3 moles of dicarboxylic acid, about 1 mole of tricarboxylic acid, about 2 moles of tricarboxylic acid, and about 3 moles of tricarboxylic acid, under a condition selected from the group consisting of under a vacuum, under an inert gas blanket, and in the presence of a high boiling solvent, until the reaction is complete.

19. A process for inhibiting corrosion comprising applying the composition according to claim 4 to a substrate in need of corrosion protection.

20. The method of claim 3 wherein the melt has a temperature ranging from 120° C. to 180° C.

* * * * *